United States Patent [19]

Mikkelsen

[11] Plant 4,262

[45] June 13, 1978

[54] IMPATIENS PLANT

[75] Inventor: James C. Mikkelsen, Ashtabula, Ohio

[73] Assignee: Mikkelsens Inc., Ashtabula, Ohio

[21] Appl. No.: 786,849

[22] Filed: Apr. 12, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

An impatiens plant with excellent self-branching, soft pink flower color, green foliage with variegated zones of yellow color, and adaptability to outdoor or potted plant growth.

1 Drawing Figure

The present invention relates to a new and distinctive cultivar of impatiens plant, botanically known as impatiens and known by the cultivar name Freedom. The new cultivar was developed by me through controlled breeding by crossing Mikkelsen seedling 74-133-1 (seed parent) with Mikkelsen seedling 73-26 (pollen parent), both of which are unpatented cultivars. Asexual reproduction of terminal or stem cuttings has shown that the unique features of this new impatiens cultivar are stabilized and are reproduced true to type in successive propagations.

The following characteristics distinguish the new impatiens from both its parent varieties and other cultivated impatiens of this type known and used in the floriculture industry:

1. There is a similar appearance in plant form of Freedom to my cultivars Paul Revere, Lafayette, Preamble and Liberty since they were all selected for low, compact, self-branching characteristics suitable for pot plant culture or for outdoor plantings. The cultivar Paul Revere is disclosed in my pending application Ser. No. 764,525; Lafayette is disclosed in my pending application Ser. No. 764,023; Preamble is disclosed in my pending application Ser. No. 764,024, and Liberty is disclosed in my pending application Ser. No. 764,531, all of which applications were filed on Jan. 31, 1977.

2. In comparing Freedom to Preamble, the flower color of Freedom is a lighter, softer shade of pink.

3. The foliage of Freedom compared to Preamble is a different shade of green with more distinctive, sharper variegation zones of a cleaner yellow color.

4. In Preamble, the flower shape is nearly symmetrical whereas the top petal of the flowers of Freedom is nearly separated and the two lower petals tend to be convex along the mid-rib.

5. The throat of the flower has a deeper tone than the petals.

6. When tested outdoors in the summer of 1976 by planting small plants from 4" pots in early June, Freedom was second only to Preamble in overall quality, being 24"-30" in diameter by self-branching, without any indications of botrytis infection, and having excellent expression of variegated foliage. Plants were in excellent condition in every respect until the killing frost of late October.

7. As a potted plant, Freedom grows very well and has better than average keeping qualities for the foliage.

8. The group of aforementioned New Guinea hybrids, including Freedom, planted in full sunlight, regularly watered, and supplied with balanced nutrients have been better quality garden plants than most varieties of petunias or geraniums, grown under the same conditions.

The accompanying colored photographic drawing illustrates the overall appearance of the new cultivar, with the colors being as true as it is reasonably possible to obtain in a colored reproduction of this type. The photograph was taken in March 1977, and the plant grown in a 5" pot was approximately 8" above the top of the pot and was 18" in diameter.

The following is a detailed description of my new impatiens cultivar based on plants produced under commercial practices in the greenhouses of Mikkelsens Inc., Ashtabula, Ohio. Color references are made to the Royal Horticultural Society Colour Chart except where general terms of ordinary dictionary significance are used.

PARENTAGE

A controlled cross of Mikkelsen seedling 74-133-1 as the seed parent crossed with Mikkelsen seedling 73-26 as the pollen parent.

PROPAGATION

Type cutting: Terminal vegetative cuttings 2–3 cm. long.

Time to visible rooting: 10 days at 21° C summer, 15 days at 20° C winter.

Rooting habit: Typical for New Guinea impatiens, being rapid, profuse in both primary and secondary roots, dendritic.

PLANT DESCRIPTION

Form: Short compact bushy herb, self branching.

Habit of growth: Slow to medium rate of growth, tending to be procumbent, spreading, self branching with strong vigorous stems.

Foliage description: Firm dark green leaves, generally 6 per node, internodal distance approximately 2 cm.; firm texture, extremely durable to outdoor conditions in Ohio.

*Size.*—Up to 5 cm. wide by 12 cm. long with petiole up to 3 cm. long.

*Shape.*—Symmetrically elliptical, apex acuminate, base between cuneate and acute, slightly revolute.

*Texture.*—Firm, leathery, glabrous, rugose.

*Margin.*—Entire, very slightly ciliolate.

*Color.*—Young foliage, top side green nearly 139-A, under side reddish overtone; mature foliage, top side outer area green between 139-A and 147A, inner area yellow orange 16B, under side diffuse green and yellow.

*Venation.*—Pinnately, arcuate.

FLOWERING DESCRIPTION

Flowering habits: Generally one flower per leaf, opening sequentially around the node as the leaves develop, with 2–4 flowers being open at each node at one time. With well developed self branching plants, flowering is considered profuse.

Natural flowering season: Flowering is indeterminant, occurring at all times of the year.

Flower bud description: Immature buds are pyramidal, deep maroon color. As buds open, two true sepals separate, the top petal being covered with a sepal-like structure; a hollow nearly white spur emerges from a lower internal sepal-like structure.

Flowers borne: Individually on a nearly white pedicel approximately 4 cm. long by 2 mm. in diameter at its base.

Quantity of flowers: Typical for New Guinea impatiens, having one flower per leaf but appearing profuse because of many nodes present due to frequent self-branching.

Petals:

*Shape.*—Top petal has scale-like sepal on underside, separated from side petals, lower petals larger, apice indented.

*Color.*—Top side in winter when opening in the greenhouse red 56B, with center vein and base red between 55A–B fading to nearly white except throat being red 55D; underside more intense to generally 52C.

*Number of petals.*—Five.

*Size of petals.*—2×3 cm., flower diameter up to 6 cm.

*Curved white spur.*—6 cm. lg.

Reproductive organs:

*Stamens.*—One in number. (a) Anther shape: Hooded, color light red 55B to white. (b) Pollen color: White.

*Pistils.*—(a) Stigma shape: Flat, circular, irregular surface, color crystalline light green. (b) Style color: Green. (c) Ovaries: One in number, size 4 mm., color green; produces viable heterozygous seed.

DISEASE RESISTANCE

Shows strong resistance to botrytis and to mites.

I claim:

1. A new and distinct cultivar of impatiens plant known by the cultivar name Freedom and particularly characterized as to uniqueness by the combined characteristics of low, compact, self-branching characteristics; soft pink flower color, green foliage with distinctive, variegated zones of yellow color; separated top and lower flower petals, with the color in the throat being of a deeper tone than the petals; excellent outdoor growth characteristics, and excellent keeping qualities as a potted plant.

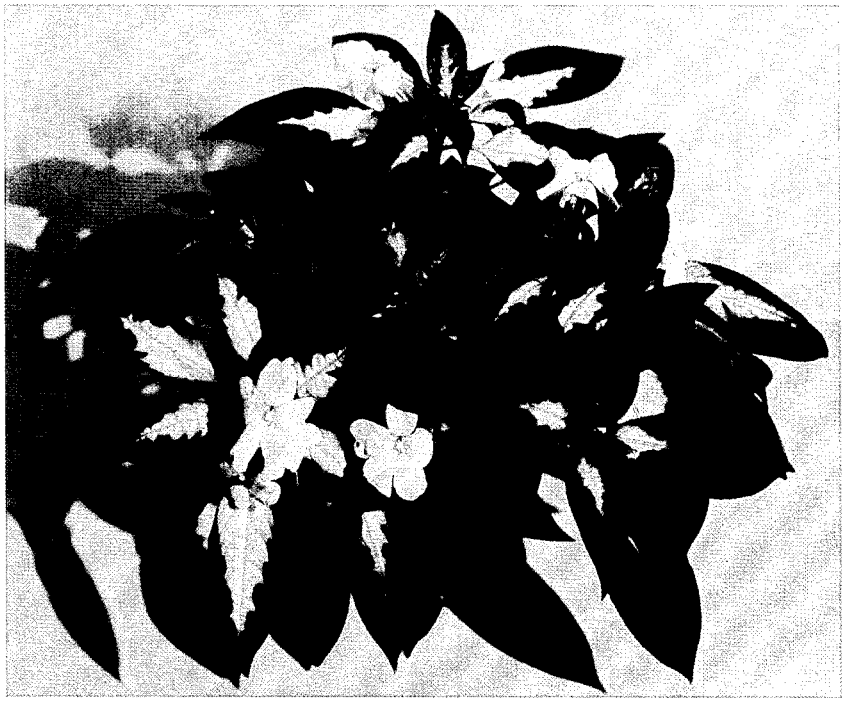

* * * * *